(12) United States Patent
Crowley

(10) Patent No.: US 6,383,209 B1
(45) Date of Patent: May 7, 2002

(54) SHEATH FOR TISSUE SPECTROSCOPY

(75) Inventor: Robert J. Crowley, Sudbury, MA (US)

(73) Assignee: Boston Scientific Corporation, Natick, MA (US)

( * ) Notice: Subject to any disclaimer, the term of this patent is extended or adjusted under 35 U.S.C. 154(b) by 142 days.

(21) Appl. No.: 09/585,188

(22) Filed: Jun. 1, 2000

Related U.S. Application Data

(63) Continuation of application No. 08/939,707, filed on Sep. 29, 1997, now Pat. No. 6,096,065.

(51) Int. Cl.[7] .................................................. A61N 5/06
(52) U.S. Cl. ......................... 607/88; 600/478; 600/121; 600/310
(58) Field of Search .................. 607/88–89; 606/15–17; 600/115, 121, 125, 310, 476–478

(56) References Cited

U.S. PATENT DOCUMENTS

| | | | |
|---|---|---|---|
| 2,002,559 A | | 5/1935 | Wappler |
| 2,583,937 A | | 1/1952 | Fossati |
| 3,176,114 A | | 3/1965 | Kneisley |
| 3,469,685 A | * | 9/1969 | Baermann |
| 4,197,944 A | * | 4/1980 | Catlin |
| 4,233,493 A | | 11/1980 | Nath |
| 4,274,706 A | | 6/1981 | Tangonan |
| 4,289,966 A | | 9/1981 | Roberts |
| 4,340,307 A | | 7/1982 | Diamond et al. |
| 4,349,031 A | * | 9/1982 | Perlin |

(List continued on next page.)

FOREIGN PATENT DOCUMENTS

| | | |
|---|---|---|
| DE | 888727 | 7/1949 |
| DE | 30 23 130 | 1/1982 |
| DE | 40 05 743 | 8/1991 |
| DE | 195 12 518 | 10/1995 |
| EP | 0 314 937 | 10/1988 |
| EP | 0 304 321 | 9/1992 |
| EP | 0 629 380 | 12/1994 |
| EP | 0 650 694 A1 | 5/1995 |
| EP | 0 728 440 | 8/1996 |
| EP | 0 777 119 | 6/1997 |

(List continued on next page.)

OTHER PUBLICATIONS

Petrofsky, "In Vivo Measurement of Brain Blood Flow in the Cat," *IEEE Transactions on Biomedical Engineering;* vol. BME–26, No. 8: 441–445 (Aug., 1979).

Internet Publication, http://iqe.ethz.ch/~fpst/Final_Report/M4/M4PO4–1.html.

Kopp et al., "Stay Tuned: Photonic Filters Color Your World," *Photonics Spectra,* Mar. 1997, pp. 125–129.

Coleman et al., "Acoustic Emission and Sonoluminescence Due to Cavitation at the Beam Focus of an Electrohydraulic Shock Wave Lithotripter", *Ultrasound in Med. Biol,* vol. 18, No. 3, pp. 267–281 (1992).

Vona et al., "A Test of the Hypothesis that Cavitation at the Focal Area of an Extracorporeal Shock Wave Lithotripter Produces Far Ultraviolet and Soft X–Ray Emissions", *J. Acoust. Soc. Am.,* vol. 98 (2), pp. 706–711, (Aug. 1995).

(List continued on next page.)

*Primary Examiner*—Roy Gibson
(74) *Attorney, Agent, or Firm*—Testa, Hurwitz & Thibeault, LLP

(57) ABSTRACT

A sheath for use with an interventional device for tissue spectroscopy within a body includes a substantially cylindrical, flexible body having an open proximal end and a closed distal end. The flexible body securely receives interventional device via an interference fit. At least the distal end of the flexible body is formed of a material substantially transmissive of at least one of ultraviolet or visible light. For example, the material can be a polymeric materials such as polyurethane, polyethylene or polystyrene. The sheath can be disposable.

38 Claims, 4 Drawing Sheets

U.S. PATENT DOCUMENTS

| | | | |
|---|---|---|---|
| 4,472,728 A | | 9/1984 | Grant et al. |
| 4,541,272 A | | 9/1985 | Bause |
| 4,548,505 A | | 10/1985 | Ono |
| 4,556,057 A | | 12/1985 | Hiruma et al. |
| 4,569,344 A | | 2/1986 | Palmer |
| 4,570,638 A | | 2/1986 | Stoddart et al. |
| 4,672,972 A | | 6/1987 | Berke |
| 4,718,417 A | | 1/1988 | Kittrell et al. |
| 4,741,326 A | * | 5/1988 | Sidall et al. ................. 600/123 |
| 4,782,819 A | * | 11/1988 | Adair |
| 4,872,458 A | | 10/1989 | Kanshira et al. |
| 4,882,623 A | | 11/1989 | Uchikubo |
| 4,894,547 A | | 1/1990 | Leffell et al. |
| 4,902,896 A | | 2/1990 | Fertig, Sr. et al. |
| 4,928,172 A | | 5/1990 | Uehara et al. |
| 4,930,516 A | | 6/1990 | Alfano et al. |
| 4,938,602 A | | 7/1990 | May et al. |
| 4,981,138 A | | 1/1991 | Deckelbaum et al. |
| 5,001,556 A | | 3/1991 | Nakamura et al. |
| 5,009,655 A | | 4/1991 | Daignault, Jr. et al. |
| 5,019,075 A | * | 5/1991 | Spears et al. ................... 606/7 |
| 5,021,888 A | | 6/1991 | Kondou et al. |
| 5,034,010 A | | 7/1991 | Kittrell et al. |
| 5,036,853 A | | 8/1991 | Jeffcoat et al. |
| 5,042,494 A | | 8/1991 | Alfano |
| 5,045,056 A | | 9/1991 | Behl |
| 5,056,503 A | | 10/1991 | Nagasaki et al. |
| 5,062,428 A | | 11/1991 | Chance |
| 5,106,387 A | | 4/1992 | Kittrell et al. |
| 5,115,137 A | | 5/1992 | Andersson-Engels et al. |
| 5,116,759 A | | 5/1992 | Klainer et al. |
| 5,125,404 A | | 6/1992 | Kittrell et al. |
| 5,127,407 A | | 7/1992 | Tan |
| 5,131,398 A | | 7/1992 | Alfano et al. |
| 5,166,755 A | | 11/1992 | Gat |
| 5,172,693 A | | 12/1992 | Doody |
| 5,174,297 A | | 12/1992 | Daikuzono |
| 5,187,572 A | | 2/1993 | Nakamura et al. |
| 5,197,672 A | | 2/1993 | Chance et al. |
| 5,190,538 A | * | 3/1993 | Hussein et al. |
| 5,193,542 A | | 3/1993 | Missanelli et al. |
| 5,197,470 A | | 3/1993 | Helfer et al. |
| 5,201,318 A | | 4/1993 | Rava et al. |
| 5,206,174 A | | 4/1993 | Gehrke et al. |
| 5,213,569 A | | 5/1993 | Davis |
| 5,233,621 A | | 8/1993 | Lawandy |
| 5,242,437 A | | 9/1993 | Everett et al. |
| 5,261,410 A | | 11/1993 | Alfano et al. |
| 5,262,645 A | | 11/1993 | Lambert et al. |
| 5,304,173 A | | 4/1994 | Kittrell et al. |
| 5,305,748 A | | 4/1994 | Wilk |
| 5,309,907 A | | 5/1994 | Fang et al. |
| 5,318,024 A | | 6/1994 | Kittrell et al. |
| 5,335,663 A | * | 8/1994 | Oakley et al. |
| 5,348,018 A | | 9/1994 | Alfano et al. |
| 5,350,375 A | | 9/1994 | Deckelbaum et al. |
| 5,351,532 A | | 10/1994 | Hager |
| 5,377,676 A | | 1/1995 | Vari et al. |
| 5,383,467 A | | 1/1995 | Auer et al. |
| 5,383,928 A | | 1/1995 | Scott et al. |
| 5,386,827 A | | 2/1995 | Chance et al. |
| 5,398,844 A | | 3/1995 | Zaslavsky et al. |
| 5,402,778 A | | 4/1995 | Chance |
| 5,402,792 A | | 4/1995 | Kimura |
| 5,404,881 A | * | 4/1995 | Cathaud et al. |
| 5,405,369 A | | 4/1995 | Selman et al. |
| 5,408,992 A | * | 4/1995 | Hamlin et al. |
| 5,413,108 A | | 5/1995 | Alfano |
| 5,417,207 A | | 5/1995 | Young et al. |
| 5,419,323 A | | 5/1995 | Kittrell et al. |
| 5,421,337 A | | 6/1995 | Richards-Kortum et al. |
| 5,421,339 A | | 6/1995 | Ramanujam et al. |
| 5,443,781 A | * | 8/1995 | Saab .......................... 264/291 |
| 5,445,608 A | | 8/1995 | Chen et al. |
| 5,452,723 A | | 9/1995 | Wu et al. |
| 5,456,252 A | | 10/1995 | Vari et al. |
| 5,461,229 A | | 10/1995 | Sauter et al. |
| 5,467,767 A | | 11/1995 | Alfano et al. |
| 5,512,757 A | | 4/1996 | Cederstrand et al. |
| 5,517,313 A | | 5/1996 | Colvin, Jr. |
| 5,527,281 A | | 6/1996 | Haas |
| 5,542,928 A | | 8/1996 | Evans et al. |
| 5,545,897 A | | 8/1996 | Jack |
| 5,553,614 A | | 9/1996 | Chance |
| 5,555,885 A | | 9/1996 | Chance |
| 5,556,421 A | | 9/1996 | Prutchi et al. |
| 5,562,100 A | | 10/1996 | Kittrell et al. |
| 5,571,152 A | | 11/1996 | Chen et al. |
| 5,579,773 A | | 12/1996 | Vo-Dinh et al. |
| 5,582,161 A | | 12/1996 | Kee |
| 5,632,740 A | | 5/1997 | Koch et al. |
| 5,647,368 A | | 7/1997 | Zeng et al. |
| 5,769,791 A | | 6/1998 | Benaron et al. |
| 5,785,658 A | | 7/1998 | Benaron et al. |
| 5,807,261 A | | 9/1998 | Benaron et al. |
| 5,830,146 A | * | 11/1998 | Skladnev et al. |
| 5,836,918 A | | 11/1998 | Dondlinger |
| 5,863,287 A | * | 1/1999 | Segawa ...................... 600/121 |

FOREIGN PATENT DOCUMENTS

| | | |
|---|---|---|
| EP | 0 792 618 | 9/1997 |
| JP | 02-223828 | 9/1990 |
| JP | 07-88105 | 4/1995 |
| JP | 07-289506 | 11/1995 |
| JP | 08-83569 | 3/1996 |
| JP | 9-192138 | 7/1997 |
| WO | WO 90/04352 | 5/1990 |
| WO | WO 90/12536 | 11/1990 |
| WO | WO 91/15151 | 10/1991 |
| WO | WO 92/14514 | 9/1992 |
| WO | WO 92/15253 | 9/1992 |
| WO | WO 94/13191 | 6/1994 |
| WO | WO 95/12349 | 5/1995 |
| WO | WO 96/05693 | 2/1996 |
| WO | WO 96/07451 | 3/1996 |
| WO | WO 96/24406 | 8/1996 |
| WO | WO 96/39932 | 12/1996 |
| WO | WO 97/01985 | 1/1997 |
| WO | WO 98/22805 | 5/1998 |

OTHER PUBLICATIONS

Cothren et al., "Gastrointestinal Tissue Diagnosis by Laser–Induced Fluorescence Spectroscopy at Endoscopy" *Gastro Endoscopy,* vol. 36, No. 2, pp. 105–111, 1990.

Kapadia et al, "Laser–induced fluorescence spectroscopy of human colonic mucosa", *Gastroentrerology,* vol. 29, pp. 150–157, 1990.

Lilge et al., "Light Induced Fluorescennce Spectroscopy at Endoscopy", Presented at the 10th Asisan Pacific Congress of Gastroenterology, 1996.

Huang et al., "Fluorescence Diagnosis of Gynecological Cancerous and Normal Tissues", *SPIE,* vol. 2135, pp. 42–44, 1994.

Anidjar et al., "Ultraviolet Laser–Induced Autofluorescence Distinction Between Malignant and Normal Urothelial Cells and Tissues", *Journal of Biomedical Optics,* vol. 1 No.3, pp. 335–341, 1996.

Crowley et al., "Ultrasound Guided Therapeutic Catherters: Recent Developments and Clinical Results", *The International Journal of Cardiac Imaging,* vol. 6, pp. 145–156, 1991.

Meindi, J. Implantable Telemetry in Biomedical Research, Electronics Engineers' Handbook, McGraw–Hill 1989, pp 26–41—25–53.

Ko, Biomedical Sensors and Actuators, Electronics Engineers' Handbook, McGraw–Hill 1989, pp 26–53—26–68.

International Search Report for PCT/US97/20367.

International Search Report for PCT/US97/20435.

International Search Report for PCT/US97/20324 dated Mar. 11, 1998.

International Search Report for PCT/US98/20019 dated Jan. 20, 1999.

International Search Report for PCT/US98/20018 dated Jan. 21, 1999.

International Search Report for PCT/US98/21100 dated Feb. 8, 1999.

* cited by examiner

SHEATH FOR TISSUE SPECTROSCOPY

This application is a continuation of U.S. patent application Ser. No. 08/939,707 filed Sep. 29, 1997, now U.S. Pat. No. 6,096,065, issued on Aug. 1, 2000 the entire disclosure of which is incorporated herein by reference.

FIELD OF THE INVENTION

The invention relates generally sheaths for use with interventional devices within a body. More particularly, the invention relates to a sheath, which is substantially transmissive of ultraviolet and/or visible light, for use with an interventional device for tissue spectroscopy within a body.

BACKGROUND OF THE INVENTION

Tissue spectroscopy, which can include optical biopsy procedures, is a relatively new field in which light waves are used to diagnose diseases in the human body. Systems for performing such procedures typically include one or more light sources that illuminate the tissue and one or more receiving channels that measure or map the resulting emission from illuminated tissue. Interventional devices for performing such procedures can take on many forms. A common form is a long fiber-equipped catheter with a proximally mounted connector and a distal tip that is capable of sending and receiving light through optical transmission. Another form is a probe, which can contain a light source and detector, that can be placed in a body cavity. Examples of such probes are provided in commonly owned, copending U.S. patent application entitled, "Miniature Spectrometer" by Robert J. Crowley, Ser. No. 08/898,604, which is incorporated herein by reference. Within these probe-style spectroscopic devices, it is possible to include an entire power supply, light emission system, light detection system, and readout within the device. Such probes can be disposable using mass production techniques.

There are, however, situations in which repeated use of the probe is desirable. Such situations can include calibration, test and application of the probe to various areas of the body. The related problems of probe contamination and disease transfer should be avoided whenever possible. It has been suggested that condoms can be used as a sheath over such probes to prevent the occurrence of these problems. One problem associated with condoms and many other known sheath materials is that they often attenuate energy in the diagnostic wavelength bands, including the visible and ultraviolet wavelength ranges that are useful for detecting cancer and other life threatening diseases.

SUMMARY OF THE INVENTION

It is therefore an object of the present invention to provide a sheath for use with an interventional device which is substantially transmissive of wavelengths used in tissue spectroscopy. It is another object of the invention to provide a sheath shaped to provide optimal optical contact with tissue under examination while affording good light transmission characteristics. It is yet another object of the invention to provide a sheath that can be contoured using a pressurizable fluid so that optimal contact with various tissue and organs shapes can be achieved. It is yet another object of the invention to provide a sheath with an optically transmissive distal end constructed to provide better transmission capability and to provide a filter function to enhance the spectroscopic procedure.

In one aspect, the present invention features a sheath for use with an interventional device for diagnostic procedures in a body. The interventional device can include, without limitation, a catheter, an endoscope, a guide wire, a needle or an introducer. The diagnostic procedures can include tissue spectroscopy or, more specifically, in vivo optical biopsy procedures.

The sheath comprises a flexible body having an open proximal end and a closed distal end. The sheath can be cylindrically shaped to securely receive the interventional device via an interference fit. At least the distal end of the flexible body is formed of a material substantially transmissive of ultraviolet and/or visible light. The material can be, for example, a polymeric material such as polyurethane, polyethylene or polystyrene. A quartz window, which is substantially transmissive of ultraviolet and/or visible light, can be disposed on the distal end of the flexible body. The sheath can be disposable.

In a detailed embodiment, the sheath can also comprise a fluid chamber and a channel. The fluid chamber is located at the distal end of the flexible body. The channel extends from the proximal end to the distal end of the flexible body and provides fluid to the fluid chamber. The fluid chamber can be filled to provide optimal optical contact between the interventional device and the tissue under examination. The distal end of the flexible body can be formed of a material and/or have a thickness optimized to selectively filter energy emitted from tissue in the body at predetermined wavelengths (e.g., below 280 nm and above 500 nm)

In another aspect, the invention features an interventional device for tissue spectroscopy and in vivo optical biopsy procedures. The device includes an endoscopic probe and a sheath. The probe is insertible into an orifice of a body. The sheath comprises a flexible body having an open proximal end and a closed distal end. At least the distal end of the flexible body is formed of a material substantially transmissive of ultraviolet and/or visible light (e.g., polyurethane, polyethylene or polystyrene). A quartz window can be disposed on the distal end of the flexible body. The sheath can also comprise a fluid chamber and a channel for providing optimal optical contact between the interventional device and the tissue under examination.

DETAILED DESCRIPTION

The present invention features selectively transmissive sheaths for use with interventional devices insertible into body cavities to protect users and patients from biological contamination and the transfer of disease. The sheaths have visible and/or ultraviolet transmission characteristics resulting in reduced attenuation of light at diagnostic wavelengths for tissue spectroscopy and optical biopsy procedures. Advantages of using a sheath covering with a reuseable probe include inherent disposability and low cost. Representative applications for the sheath covered probe include cervix procedures and intraoperative uses.

Figure 1:
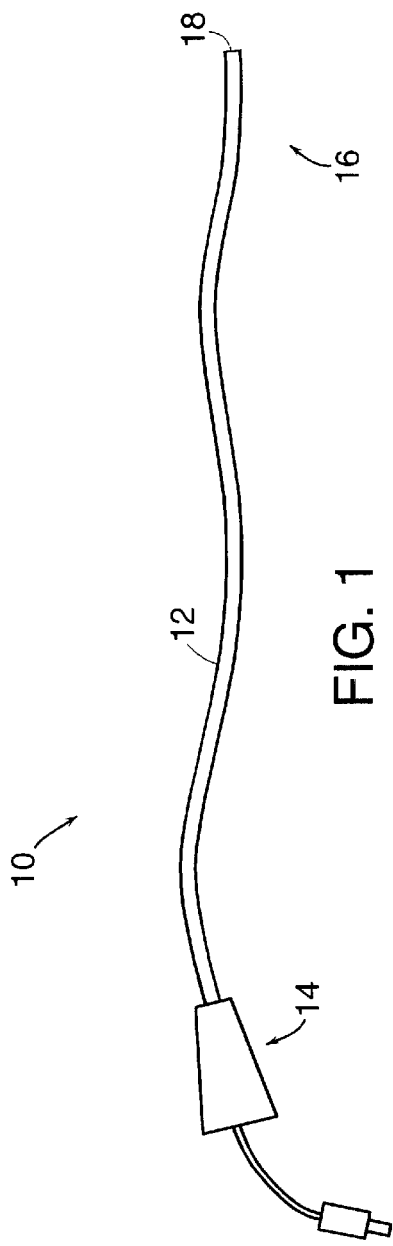
FIG. 1 illustrates a prior art probe for tissue spectroscopy and optical biopsy procedures.

FIG. 1 illustrates a prior art endoscopic probe 10 for tissue spectroscopy and optical biopsy procedures has a body 12 with a proximal end 14 and a distal end 16. The probe body includes light carrying fibers (not shown) and has an aperture 18 at the distal end 16 for coupling light energy from the probe into a region of interest in the body of a patient.

Figure 2:
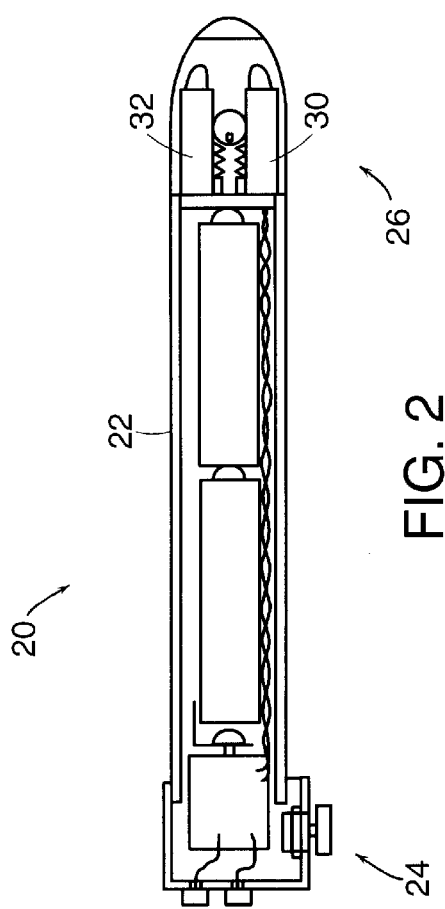
FIG. 2 illustrates a self-contained probe for tissue spectroscopy and optical biopsy procedures.

FIG. 2 illustrates a self-contained endoscopic probe 20 for tissue spectroscopy and optical biopsy. The probe 20 has a body 22 with a proximal end 24 and a distal end 26. The probe 20 does not require fibers for transmitting optical energy through the body 22, but instead includes a light emitter 30 and detector 32 located at or near the distal end 26. This probe is described in commonly owned, copending U.S. patent application, entitled "Portable Tissue Spectroscopy Apparatus" by Robert J. Crowley and Mark Hamm, which is incorporated herein by reference.

Figure 3A:
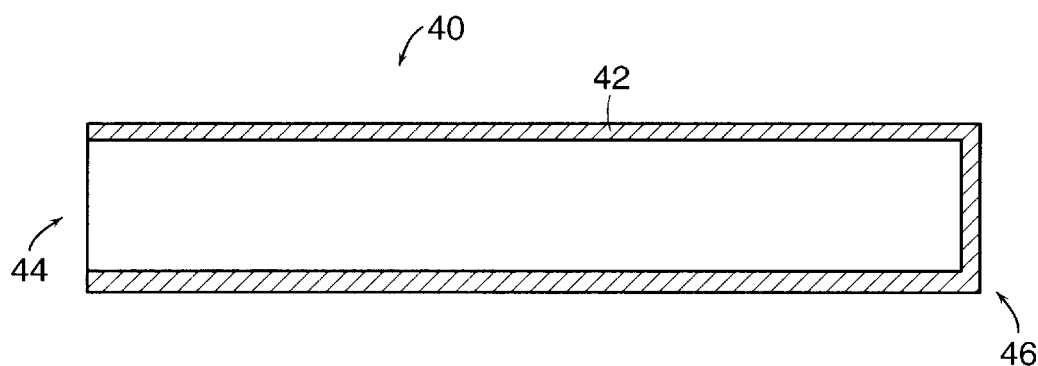
FIG. 3a is a cross-sectional view of a sheath incorporating the principles of the invention.

FIG. 3a illustrates a sheath 40 incorporating the principles of the invention. The sheath 40 comprises a flexible body 42 having an open proximal end 44 and a closed distal end 46. The sheath 40 can be cylindrically shaped and is secured over an interventional device, such as the probes shown in FIGS. 1 and 2, via an interference fit. In one embodiment, at least the distal end 46 of the flexible body 42 is formed of a material substantially transmissive of ultraviolet and/or visible light. In another embodiment, the distal end of the flexible body can be formed of a material and/or have a thickness optimized to selectively filter energy emitted from tissue in the body at predetermined wavelengths (e.g., below 280 nm and above 500 nm). In yet another embodiment, the flexible body 42 is formed of a material substantially transmissive of ultraviolet and/or visible light. The material can be a polymeric materials such as polyurethane, polyethylene or polystyrene.

Figure 3B:
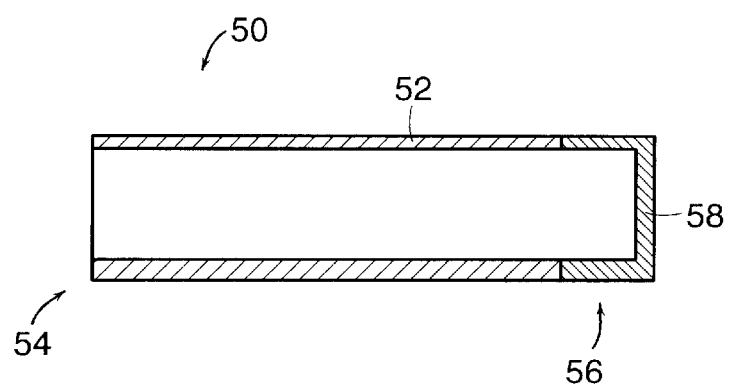
FIG. 3b is a cross-sectional view of a sheath with a window at the distal end.

FIG. 3b illustrates a sheath 50 comprising a flexible body 52 having an open proximal end 54 and a closed distal end 56. The sheath 40 can be cylindrically shaped and includes a quartz window 58, which is substantially transmissive of ultraviolet and/or visible light, on the distal end of the flexible body 52.

With reference to FIGS. 3a and 3b, the sheath can have a wall thickness on the order of a few thousands of an inch. For example, a typical thickness can be on the order of 3–10 thousands of an inch. This range is consistent with that of ordinary plastic films, such as polyethylene, which have good optical transmission properties, good strength, and are pinhole free so that body fluids do not leak through and contaminate the probe.

The distal end of the sheath can be formed to have a rounded shape to conform to a round probe tip, although any other shape can be formed. Any one of a variety of methods of forming the shape of the distal end of the sheath can be used. For example, the distal end can be preformed over a mandrel during the manufacturing process of the sheath. Another example is to have a general shape and use the plastic properties of the sheath material to contour the distal end by placing the sheath over the probe during use. To accomplish the latter, some force must be applied to the flexible body to cause the sheath material to stretch. A proximal band (not shown) allows the stretching process to take place without elastic recoil.

Figure 4:
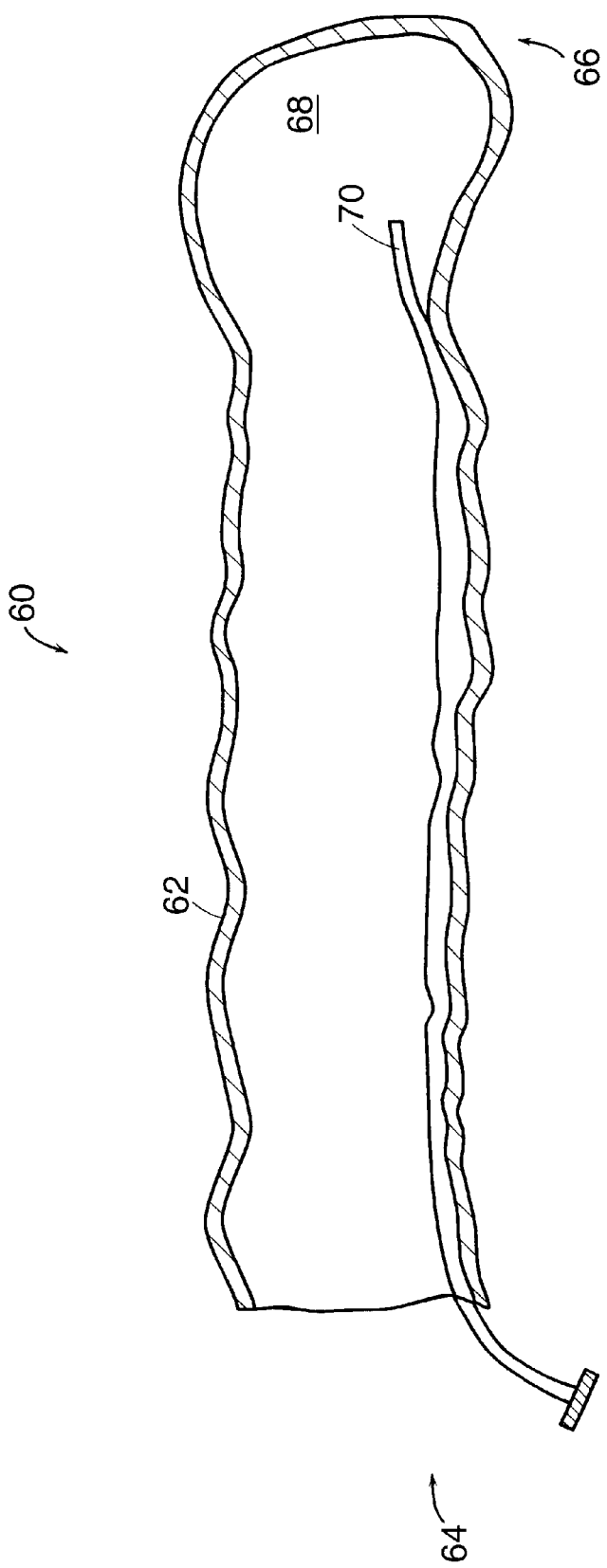
FIG. 4 is a cross-sectional view of a sheath with a fluid chamber and an inflation channel.

FIG. 4 shows a sheath 60 having a flexible body 62 and an open proximal end 64 and a closed distal end 66. The sheath 60 also includes a fluid chamber 68 and an inflation channel 70. The fluid chamber 68 is located at the distal end 68 and receives fluid (e.g., water) from the fluid channel 70, which extends from the proximal end 64 to the distal end 66 of the flexible body 62. Once the sheath 60 is placed over a probe (not shown), the fluid chamber is filled to provide optimal optical contact between the probe and the tissue under examination.

Figure 5:
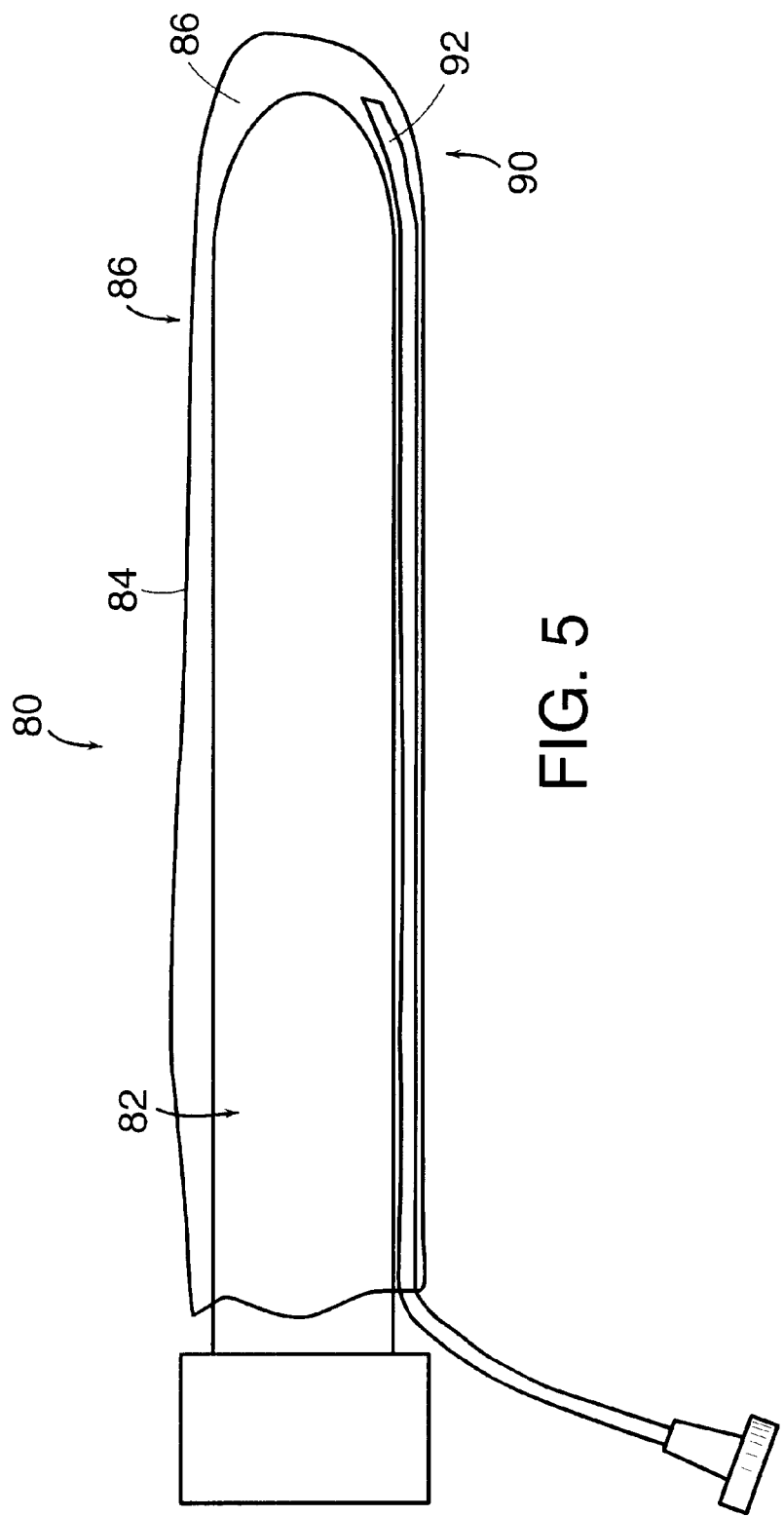
FIG. 5 illustrates a self-contained interventional device including an endoscopic probe covered by a sheath for tissue spectroscopy and in vivo optical biopsy procedures.

FIG. 5 shows a self-contained interventional device 80 for tissue spectroscopy and in vivo optical biopsy procedures. The device 80 includes an endoscopic probe 82 is insertible into an orifice of a body. The probe 82 is securely disposed within the flexible body 84 of a disposable sheath 86. The sheath 86 is formed of a material substantially transmissive of ultraviolet and/or visible light (e.g., polyurethane, polyethylene or polystyrene). The sheath 84 includes a fluid chamber 88 at its distal end 90 and a channel 92 for filling the chamber.

Equivalents

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A removable sheath for providing repeated use of an interventional device for tissue spectroscopy in a mammalian body orifice having a contour, the sheath comprising:

a flexible body having an open proximal end and a closed distal end, said flexible body being sized and shaped to receive the interventional device and to be removed from the device, said flexible body being conformable to the contour of the orifice, the distal end of the flexible body comprising a window that is substantially transmissive of an ultraviolet light;

a fluid chamber located at the distal end of the flexible body; and a channel extending from the proximal end to the distal end of the flexible body for providing fluid to the fluid chamber, wherein the fluid chamber receives a fluid through the channel to facilitate optical contact between the sheath and a tissue under examination.

2. The sheath of claim 1 wherein said window is more transmissive of ultraviolet light than the rest of the flexible body.

3. The sheath of claim 1 wherein the window comprises quartz.

4. The sheath of claim 1 wherein the flexible body is between about 0.003 inch and about 0.010 inch thick.

5. The sheath of claim 1 wherein the flexible body is sized and shaped to securely receive the interventional device via an interference fit.

6. The sheath of claim 1 wherein the flexible body selectively filters light emitted from the tissue at predetermined wavelengths.

7. The sheath of claim 1 wherein the flexible body is formed of a polymeric material.

8. The sheath of claim 7 wherein the flexible body is formed of at least one of polyurethane, polyethylene or polystyrene.

9. The sheath of claim 1 wherein at least the distal end of the flexible body is substantially transmissive of visible light.

10. The sheath of claim 1 wherein the flexible body is substantially cylindrical.

11. The sheath of claim 1 wherein the sheath is disposable.

12. The sheath of claim 6 wherein the flexible body filters light at wavelengths below about 280 nm and above about 500 nm.

13. The sheath of claim 1 wherein the intervention device is selected from the group consisting of a catheter, an endoscope, and an introducer.

14. A device for tissue spectroscopy comprising:

a probe insertable in an orifice of a mammalian body, the probe having a distal end and a proximal end and comprising a tissue spectroscopy apparatus positioned near the distal end, the tissue spectroscopy apparatus comprising a light source for illuminating a tissue under examination with an ultraviolet light, a light detector for detecting an optical property of the illuminated tissue, and a power source; and a removable sheath for encapsulating said probe, said sheath comprising a flexible body having an open proximal end for receiving the probe and a closed distal end, a fluid chamber located at the distal end of the flexible body, and a channel extending from the proximal end to the distal end of the flexible body for providing fluid to the fluid chamber for optimizing optical contact between the device and the tissue under examination, wherein at least the distal end of the flexible body is substantially transmissive of the ultraviolet light.

15. The device of claim 14 further comprising a window disposed on the distal end of the flexible body.

16. The device of claim 14 wherein the flexible body is between about 0.003 inch and about 0.010 inch thick.

17. The device of claim 14 wherein the flexible body selectively filters light emitted from the tissue at predetermined wavelengths.

18. The device of claim 17 wherein the flexible body filters light at wavelengths below about 280 nm and above about 500 nm.

19. The device of claim 14 wherein the flexible body is formed of a polymeric material.

20. The device of claim 19 wherein the flexible body is formed of at least one of polyurethane, polyethylene or polystyrene.

21. The device of claim 14 wherein the sheath is disposable.

22. A method of conducting tissue spectroscopy, said method comprising the steps of:

providing a device having a distal end and a proximal end and comprising a tissue spectroscopy apparatus positioned near the distal end, said tissue spectroscopy apparatus comprising a light source for illuminating a tissue under examination with an ultraviolet light;

encapsulating said device in a removable sheath, said sheath having (i) an open proximal end and a closed distal end, the distal end of the sheath comprising a window that is substantially transmissive of said ultraviolet light, (ii) a fluid chamber, and (iii) a channel extending from the proximal end of the sheath to said fluid chamber;

inserting the encapsulated device into a mammalian body orifice having a contour, until the distal end of the device is adjacent the tissue;

manipulating the encapsulated device to conform to the contour of the orifice; and injecting a fluid into said fluid chamber through said channel to facilitate optical contact between the encapsulated device and the tissue.

23. The method of claim 22, further comprising the steps of:

removing the encapsulated device from the orifice;

removing the sheath from the device; and reusing the device in tissue spectroscopy.

24. The method of claim 22, wherein said window is more transmissive of the ultraviolet light than the rest of the sheath.

25. The method of claim 22 wherein the window comprises quartz.

26. The method of claim 22 wherein the sheath is between about 0.003 inch and about 0.010 inch thick.

27. The method of claim 22 wherein the sheath selectively filters light emitted from the tissue at predetermined wavelengths.

28. The method of claim 22 wherein the sheath filters light at wavelengths below about 280 nm and above about 500 nm.

29. The method of claim 22 wherein the sheath is formed of a polymeric material.

30. A method of conducting tissue spectroscopy, said method comprising the steps of:

providing a device having a distal end and a proximal end and comprising a tissue spectroscopy apparatus positioned near the distal end, the tissue spectroscopy apparatus comprising a light source for illuminating tissue under examination with an ultraviolet light and a light detector for detecting an optical property of the illuminated tissue;

encapsulating said device in a removable sheath, said sheath having an open proximal end and a closed distal end, the distal end of the sheath comprising a window that is substantially transmissive of said ultraviolet light, and a fluid chamber, the sheath further comprising a channel extending from the proximal end of the sheath to said fluid chamber;

inserting the encapsulated device into a mammalian body orifice having a contour, until the distal end of the device is adjacent the tissue;

manipulating the encapsulated device to conform to the contour of the orifice; and injecting a fluid into said fluid chamber through said channel to facilitate optical contact between the encapsulated device and the tissue.

31. The method of claim 30, further comprising the steps of:

removing the encapsulated device from the orifice;

removing the sheath from the device; and reusing the device in tissue spectroscopy.

32. The method of claim 30, wherein the tissue spectroscopy apparatus further comprises a power source.

33. The method of claim 30, wherein said window is more transmissive of the ultraviolet light than the rest of the sheath.

34. The method of claim 30 wherein the window comprises quartz.

35. The method of claim 30 wherein the sheath is between about 0.003 inch and about 0.010 inch thick.

36. The method of claim 30 wherein the sheath selectively filters light emitted from the tissue at predetermined wavelengths.

37. The method of claim 36 wherein the sheath filters light at wavelengths below about 280 nm and above about 500 nm.

38. The method of claim 30 wherein the sheath is formed of a polymeric material.

* * * * *